(12) United States Patent
Brown et al.

(10) Patent No.: US 11,478,268 B2
(45) Date of Patent: Oct. 25, 2022

(54) JAW MEMBERS FOR SURGICAL INSTRUMENTS AND SURGICAL INSTRUMENTS INCORPORATING THE SAME

(71) Applicant: Covidien LP, Mansfield, MA (US)

(72) Inventors: Michael J. Brown, Superior, CO (US); Jason L. Craig, Loveland, CO (US); Matthias Lester, Longmont, CO (US); Matthew S. Cowley, Frederick, CO (US)

(73) Assignee: Covidien LP, Mansfield, MA (US)

( * ) Notice: Subject to any disclaimer, the term of this patent is extended or adjusted under 35 U.S.C. 154(b) by 146 days.

(21) Appl. No.: 16/993,960

(22) Filed: Aug. 14, 2020

(65) Prior Publication Data
US 2021/0045768 A1    Feb. 18, 2021

Related U.S. Application Data

(60) Provisional application No. 62/887,999, filed on Aug. 16, 2019.

(51) Int. Cl.
*A61B 17/32* (2006.01)
*A61B 17/00* (2006.01)

(52) U.S. Cl.
CPC ......... *A61B 17/320092* (2013.01); *A61B 2017/00473* (2013.01); *A61B 2017/00734* (2013.01); *A61B 2017/320075* (2017.08); *A61B 2017/320094* (2017.08)

(58) Field of Classification Search
CPC ............... A61B 17/320092; A61B 2017/320093–2017/320095
See application file for complete search history.

(56) References Cited

U.S. PATENT DOCUMENTS

| | | |
|---|---|---|
| 1,813,902 A | 7/1931 | Bovie |
| 2,235,274 A | 3/1941 | Trehern |
| 2,874,470 A | 2/1959 | Richards |
| 2,990,616 A | 7/1961 | Balamuth |
| 3,432,691 A | 3/1969 | Shoh |
| 3,489,930 A | 1/1970 | Shoh |
| 3,526,792 A | 9/1970 | Shoh |
| 3,629,726 A | 12/1971 | Popescu |

(Continued)

*Primary Examiner* — Ashley L Fishback
(74) *Attorney, Agent, or Firm* — Carter, DeLuca & Farrell LLP

(57) ABSTRACT

A surgical instrument includes a support frame defining first and second non-circular apertures each defining at least one stop surface, and a jaw member having a structural body including a proximal flange portion and an elongated distal portion extending distally from the proximal flange portion. A jaw liner is engaged with the elongated distal portion and defines a tissue-contacting surface. A first and a second pivot boss protrude from opposite sides of the proximal flange portion and at least partially into the first and second non-circular apertures, respectively. Each pivot boss is non-circular and defines at least one stop surface configured to mate with the at least one stop surface of the respective non-circular aperture to stop rotation of the jaw member before the jaw liner is forced into contact with a blade from the surgical instrument. A surgical instrument including such a jaw member is also provided.

20 Claims, 4 Drawing Sheets

(56) References Cited

U.S. PATENT DOCUMENTS

| | | | |
|---|---|---|---|
| 3,668,486 A | 6/1972 | Silver | |
| 3,809,977 A | 5/1974 | Balamuth et al. | |
| 3,875,945 A | 4/1975 | Friedman | |
| 3,924,335 A | 12/1975 | Balamuth et al. | |
| 4,012,647 A | 3/1977 | Balamuth et al. | |
| 4,193,818 A | 3/1980 | Young et al. | |
| 4,227,110 A | 10/1980 | Douglas et al. | |
| 4,300,083 A | 11/1981 | Heiges | |
| 4,302,728 A | 11/1981 | Nakamura | |
| 4,370,302 A | 1/1983 | Suzuoka et al. | |
| 4,641,053 A | 2/1987 | Takeda | |
| 5,113,116 A | 5/1992 | Wilson | |
| 5,224,680 A | 7/1993 | Greenstein et al. | |
| 5,264,925 A | 11/1993 | Shipp et al. | |
| 5,275,166 A | 1/1994 | Vaitekunas et al. | |
| 5,374,813 A | 12/1994 | Shipp | |
| 5,394,187 A | 2/1995 | Shipp | |
| 5,408,268 A | 4/1995 | Shipp | |
| 5,451,220 A | 9/1995 | Ciervo | |
| 5,490,860 A | 2/1996 | Middle et al. | |
| 5,565,520 A | 10/1996 | Fock et al. | |
| 5,582,617 A | 12/1996 | Klieman et al. | |
| 5,593,414 A | 1/1997 | Shipp et al. | |
| 5,685,311 A | 11/1997 | Hara | |
| 5,717,306 A | 2/1998 | Shipp | |
| 5,728,130 A | 3/1998 | Ishikawa et al. | |
| 5,776,155 A | 7/1998 | Beaupre et al. | |
| 5,792,138 A | 8/1998 | Shipp | |
| 5,796,056 A | 8/1998 | Bredow et al. | |
| 5,810,859 A | 9/1998 | DiMatteo et al. | |
| 5,858,018 A | 1/1999 | Shipp et al. | |
| 5,873,873 A | 2/1999 | Smith et al. | |
| 5,897,569 A | 4/1999 | Kellogg et al. | |
| 5,910,152 A | 6/1999 | Bays | |
| 5,938,633 A | 8/1999 | Beaupre | |
| 5,944,737 A | 8/1999 | Tsonton et al. | |
| 5,947,984 A | 9/1999 | Whipple | |
| 5,954,736 A | 9/1999 | Bishop et al. | |
| 5,980,510 A * | 11/1999 | Tsonton | A61B 17/320092 606/171 |
| 5,993,465 A | 11/1999 | Shipp et al. | |
| 5,994,855 A | 11/1999 | Lundell et al. | |
| 6,031,526 A | 2/2000 | Shipp | |
| 6,036,667 A | 3/2000 | Manna et al. | |
| 6,068,647 A | 5/2000 | Witt et al. | |
| 6,095,981 A | 8/2000 | McGahan | |
| 6,162,194 A | 12/2000 | Shipp | |
| 6,183,426 B1 | 2/2001 | Akisada et al. | |
| 6,220,098 B1 | 4/2001 | Johnson et al. | |
| 6,254,623 B1 | 7/2001 | Haibel, Jr. et al. | |
| 6,257,241 B1 | 7/2001 | Wampler | |
| 6,278,218 B1 | 8/2001 | Madan et al. | |
| 6,280,407 B1 | 8/2001 | Manna et al. | |
| 6,283,981 B1 | 9/2001 | Beaupre | |
| 6,284,185 B1 | 9/2001 | Tokuda et al. | |
| 6,287,344 B1 | 9/2001 | Wampler et al. | |
| 6,290,575 B1 | 9/2001 | Shipp | |
| 6,306,157 B1 | 10/2001 | Shchervinsky | |
| 6,309,400 B2 | 10/2001 | Beaupre | |
| 6,325,811 B1 | 12/2001 | Messerly | |
| 6,328,751 B1 | 12/2001 | Beaupre | |
| 6,350,269 B1 | 2/2002 | Shipp et al. | |
| 6,352,532 B1 | 3/2002 | Kramer et al. | |
| 6,416,486 B1 | 7/2002 | Wampler | |
| 6,423,082 B1 | 7/2002 | Houser et al. | |
| 6,432,118 B1 | 8/2002 | Messerly | |
| 6,443,968 B1 | 9/2002 | Holthaus et al. | |
| 6,449,006 B1 | 9/2002 | Shipp | |
| 6,454,781 B1 | 9/2002 | Witt et al. | |
| 6,454,782 B1 | 9/2002 | Schwemberger | |
| 6,458,142 B1 | 10/2002 | Faller et al. | |
| 6,480,796 B2 | 11/2002 | Wiener | |
| 6,482,220 B1 | 11/2002 | Mueller | |
| 6,491,708 B2 | 12/2002 | Madan et al. | |
| 6,500,188 B2 | 12/2002 | Harper et al. | |
| 6,514,267 B2 | 2/2003 | Jewett | |
| 6,537,291 B2 | 3/2003 | Friedman et al. | |
| 6,561,983 B2 | 5/2003 | Cronin et al. | |
| 6,565,520 B1 | 5/2003 | Young | |
| 6,588,277 B2 | 7/2003 | Giordano et al. | |
| 6,589,200 B1 | 7/2003 | Schwemberger et al. | |
| 6,607,540 B1 | 8/2003 | Shipp | |
| 6,623,500 B1 | 9/2003 | Cook et al. | |
| 6,626,926 B2 | 9/2003 | Friedman et al. | |
| 6,633,234 B2 | 10/2003 | Wiener et al. | |
| 6,652,539 B2 | 11/2003 | Shipp et al. | |
| 6,652,545 B2 | 11/2003 | Shipp et al. | |
| 6,660,017 B2 | 12/2003 | Beaupre | |
| 6,662,127 B2 | 12/2003 | Wiener et al. | |
| 6,666,875 B1 | 12/2003 | Sakurai et al. | |
| 6,678,621 B2 | 1/2004 | Wiener et al. | |
| 6,679,899 B2 | 1/2004 | Wiener et al. | |
| 6,719,776 B2 | 4/2004 | Baxter et al. | |
| 6,752,815 B2 | 6/2004 | Beaupre | |
| 6,773,444 B2 | 8/2004 | Messerly | |
| 6,869,439 B2 | 3/2005 | White et al. | |
| 6,908,472 B2 | 6/2005 | Wiener et al. | |
| 6,915,623 B2 | 7/2005 | Dey et al. | |
| 6,945,981 B2 | 9/2005 | Donofrio et al. | |
| 6,976,969 B2 | 12/2005 | Messerly | |
| 7,037,306 B2 | 5/2006 | Podany et al. | |
| 7,066,895 B2 | 6/2006 | Podany | |
| 7,074,218 B2 | 7/2006 | Washington et al. | |
| 7,108,695 B2 | 9/2006 | Witt et al. | |
| 7,128,720 B2 | 10/2006 | Podany | |
| 7,135,030 B2 | 11/2006 | Schwemberger et al. | |
| 7,163,548 B2 | 1/2007 | Stulen et al. | |
| 7,179,254 B2 | 2/2007 | Pendekanti et al. | |
| 7,179,271 B2 | 2/2007 | Friedman et al. | |
| 7,207,997 B2 | 4/2007 | Shipp et al. | |
| 7,217,128 B2 | 5/2007 | Atkin et al. | |
| 7,217,893 B1 | 5/2007 | Huang et al. | |
| 7,230,199 B2 | 6/2007 | Chou et al. | |
| 7,244,262 B2 | 7/2007 | Wiener et al. | |
| 7,269,873 B2 | 9/2007 | Brewer et al. | |
| 7,273,483 B2 | 9/2007 | Wiener et al. | |
| 7,300,446 B2 | 11/2007 | Beaupre | |
| 7,335,997 B2 | 2/2008 | Wiener | |
| 7,337,010 B2 | 2/2008 | Howard et al. | |
| 7,977,587 B2 | 7/2011 | Rajagopal et al. | |
| 8,435,258 B2 | 5/2013 | Young et al. | |
| 8,672,959 B2 | 3/2014 | Witt et al. | |
| 10,231,749 B2 * | 3/2019 | Hibner | A61B 17/320092 |
| 10,285,724 B2 * | 5/2019 | Faller | A61B 17/320092 |
| 2001/0048855 A1 | 12/2001 | Lin | |
| 2002/0002379 A1 | 1/2002 | Bishop | |
| 2002/0077645 A1 | 6/2002 | Wiener et al. | |
| 2002/0091339 A1 | 7/2002 | Horzewski et al. | |
| 2003/0144680 A1 | 7/2003 | Kellogg et al. | |
| 2003/0149424 A1 | 8/2003 | Barlev et al. | |
| 2003/0199794 A1 | 10/2003 | Sakurai et al. | |
| 2003/0212363 A1 | 11/2003 | Shipp | |
| 2004/0097972 A1 | 5/2004 | Shipp et al. | |
| 2004/0116952 A1 | 6/2004 | Sakurai et al. | |
| 2004/0256487 A1 | 12/2004 | Collins et al. | |
| 2005/0091770 A1 | 5/2005 | Mourad et al. | |
| 2005/0107658 A1 | 5/2005 | Brockway | |
| 2005/0113815 A1 | 5/2005 | Ritchie et al. | |
| 2005/0119677 A1 | 6/2005 | Shipp | |
| 2005/0149063 A1 | 7/2005 | Young et al. | |
| 2005/0203329 A1 | 9/2005 | Muto et al. | |
| 2005/0234338 A1 | 10/2005 | Masuda | |
| 2005/0234484 A1 | 10/2005 | Houser et al. | |
| 2006/0058825 A1 | 3/2006 | Ogura et al. | |
| 2006/0079878 A1 | 4/2006 | Houser | |
| 2006/0079879 A1 | 4/2006 | Faller et al. | |
| 2006/0087286 A1 | 4/2006 | Phillips et al. | |
| 2006/0129168 A1 | 6/2006 | Shipp | |
| 2006/0178579 A1 | 8/2006 | Haynes | |
| 2006/0178667 A1 | 8/2006 | Sartor et al. | |
| 2006/0194567 A1 | 8/2006 | Kelly et al. | |
| 2006/0206100 A1 | 9/2006 | Eskridge et al. | |
| 2006/0217729 A1 | 9/2006 | Eskridge et al. | |
| 2007/0011836 A1 | 1/2007 | Brewer et al. | |

(56) References Cited

U.S. PATENT DOCUMENTS

| | | |
|---|---|---|
| 2007/0149881 A1 | 6/2007 | Rabin |
| 2007/0166663 A1 | 7/2007 | Telles et al. |
| 2007/0175960 A1 | 8/2007 | Shelton et al. |
| 2007/0227866 A1 | 10/2007 | Dimig |
| 2007/0239028 A1 | 10/2007 | Houser et al. |
| 2007/0239101 A1 | 10/2007 | Kellogg |
| 2007/0282333 A1 | 12/2007 | Fortson et al. |
| 2008/0033248 A1 | 2/2008 | Akagi |
| 2008/0051693 A1 | 2/2008 | Babaev |
| 2008/0245841 A1 | 10/2008 | Smith et al. |
| 2009/0138006 A1 | 5/2009 | Bales et al. |
| 2009/0143797 A1 | 6/2009 | Smith et al. |
| 2009/0143805 A1 | 6/2009 | Palmer et al. |
| 2009/0223033 A1 | 9/2009 | Houser |
| 2009/0264909 A1 | 10/2009 | Beaupre |
| 2010/0004669 A1 | 1/2010 | Smith et al. |
| 2010/0090420 A1 | 4/2010 | Nickels, Jr. et al. |
| 2012/0078278 A1 | 3/2012 | Bales, Jr. et al. |
| 2013/0338691 A1 | 12/2013 | Young et al. |
| 2014/0107684 A1 | 4/2014 | Craig |
| 2015/0148830 A1 | 5/2015 | Stulen et al. |
| 2015/0245850 A1 | 9/2015 | Hibner et al. |
| 2016/0175001 A1 | 6/2016 | Hibner et al. |
| 2017/0119425 A1 | 5/2017 | Hibner et al. |
| 2018/0000506 A1* | 1/2018 | Hibner ............ A61B 17/320092 |

* cited by examiner

JAW MEMBERS FOR SURGICAL INSTRUMENTS AND SURGICAL INSTRUMENTS INCORPORATING THE SAME

CROSS-REFERENCE TO RELATED APPLICATIONS

This application claims the benefit of and priority to U.S. Provisional Patent Application Ser. No. 62/887,999 filed Aug. 16, 2019, the entire disclosure of which is incorporated by reference herein.

FIELD

The present disclosure relates to surgical instruments and, more particularly, to jaw members of energy-based surgical instruments and energy-based surgical instruments incorporating the same.

BACKGROUND

Many energy-based surgical instruments employ an end effector including one or more jaw members configured to facilitate clamping, manipulating, and/or applying energy to tissue to treat tissue.

Ultrasonic surgical instruments, for example, utilize ultrasonic energy in the form of ultrasonic vibrations to coagulate, cauterize, fuse, seal, cut, desiccate, fulgurate, or otherwise treat tissue. The ultrasonic energy is typically produced by a generator and transducer and is transmitted along a waveguide to an end effector of the ultrasonic surgical instrument. The end effector may include a blade that receives the ultrasonic energy from the waveguide for application to tissue and a jaw member configured to clamp tissue between the blade and the jaw member to facilitate treatment thereof.

As vibrations induced in the blade and thermal energy generated by the blade may be transferred to the jaw member, jaw members have been developed that include a jaw liner engaged to a structural body of the jaw member. While the jaw liner inhibits vibrations and thermal energy from being transferred to the structural body, the jaw liner is subject to wear from repeated and/or prolonged contact with the energized blade.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

Provided in accordance with aspects of the present disclosure is a surgical instrument including a support frame and a jaw member.

The support frame defines a first and a second non-circular aperture, each of which further define at least one stop surface. The jaw member includes a structural body, which itself further includes a proximal flange portion and an elongated distal portion extending distally from the proximal flange portion. A jaw liner is engaged with the base of the elongated distal portion and defines a tissue-contacting surface. A first and a second pivot boss protrude from opposite sides of the proximal flange portion and at least partially into the first and second non-circular apertures, respectively. Each pivot boss is non-circular and defines at least one stop surface configured to mate with the at least one stop surface of the respective non-circular aperture to stop rotation of the jaw member.

In aspects, the support frame is an inner tube extending between a handle assembly and an end effector of the surgical instrument.

In aspects, the first and second non-circular apertures are defined in a pair of support arms disposed on the distal end of the support frame.

In aspects, the first and second non-circular apertures are coupled with the first and second pivot bosses such that the first and second pivot bosses are operably connected to the pair of support arms.

In aspects, the pair of support arms are spaced apart such that the first and second non-circular apertures are transversely oriented with respect to one another.

In aspects, the first and second apertures are configured to pivotably receive the first and second pivot bosses and to allow only partial rotation of the first and second pivot bosses when coupled.

In aspects, each aperture is in the shape of a partial circle with a shelf portion in the lower distal quadrant, such that the at least one stop surface of each pivot boss will come into contact with the at least one stop surface of each aperture when rotated to prevent further closure of the jaw member.

In aspects, each pivot boss is semi-circular in shape.

In aspects, the first and second pivot bosses are configured to actuate the jaw member between an open position and a closed position, such that when the first and second pivot bosses are vertically oriented the jaw member is disposed in the open position and when the pair of pivot bosses is horizontally oriented the jaw member is disposed in the closed position.

In aspects, a separation exists between the jaw liner and the blade from the surgical instrument when disposed in the closed position.

In aspects, an interference exists between the law liner and the blade from the surgical instrument when disposed in the closed position.

A surgical instrument provided in accordance with aspects of the present disclosure includes an energy-delivering component and a jaw member positioned to oppose the energy-delivering component and movable relative thereto between an open position and a closed position for clamping tissue between the jaw member and the energy-delivering component. The jaw member may be configured similarly to any of the above aspects or as otherwise detailed herein.

In aspects, the energy-delivering component is an ultrasonic blade.

BRIEF DESCRIPTION OF THE DRAWINGS

The above and other aspects and features of the present disclosure will become more apparent in view of the following detailed description when taken in conjunction with the accompanying drawings, wherein.

DETAILED DESCRIPTION

Figure 1:
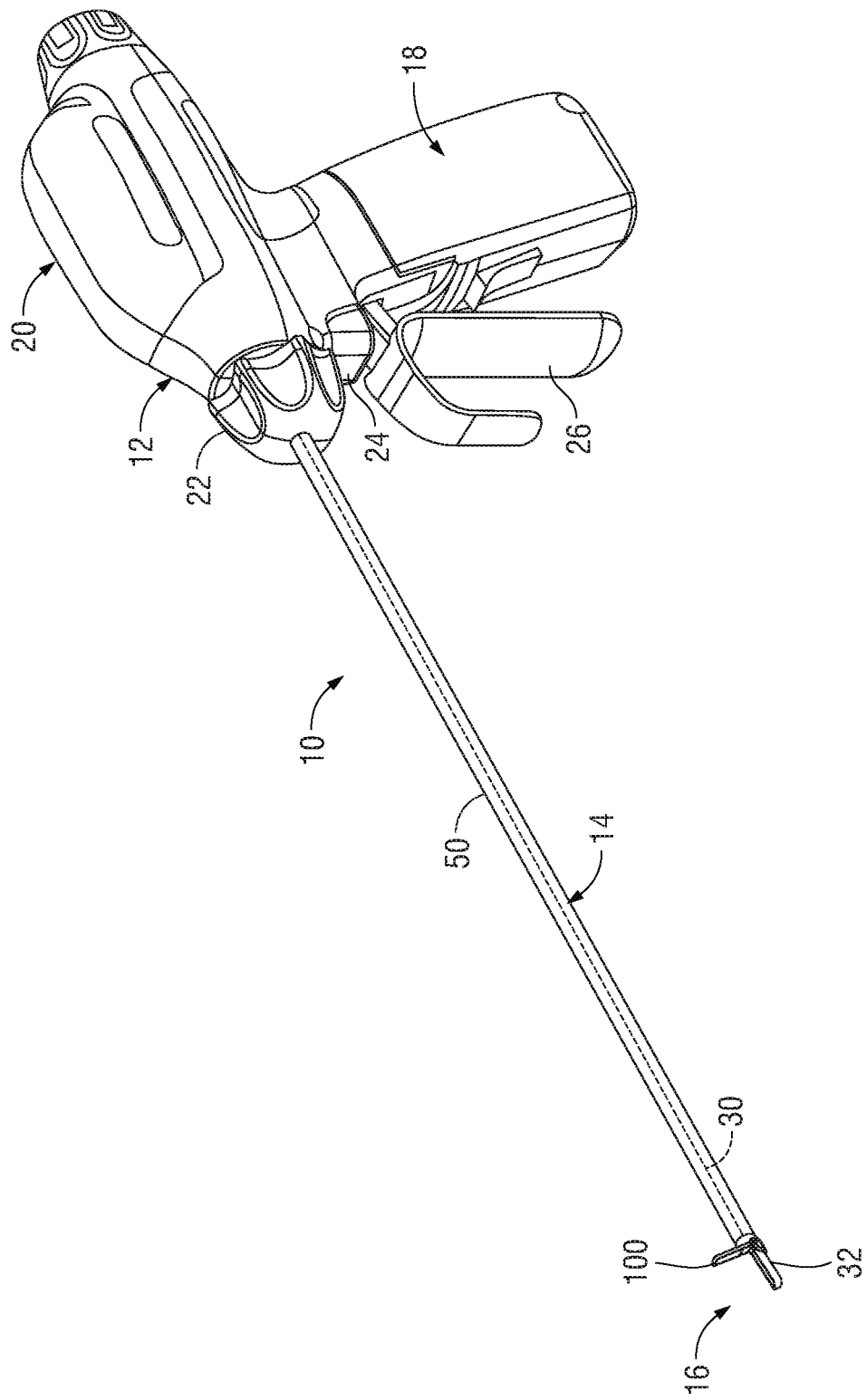
FIG. 1 is a perspective view of an ultrasonic surgical instrument including an end effector disposed in an open condition.

Jaw members and surgical instruments including such jaw members are provided in accordance with the present disclosure and detailed hereinbelow. Referring to FIG. 1, although the jaw members of the present disclosure are described for use with an ultrasonic surgical instrument 10, the jaw members of the present disclosure may alternatively be configured for use with any other suitable surgical instrument, including ultrasonic surgical instruments different from ultrasonic surgical instrument 10.

Ultrasonic surgical instrument 10 generally includes a handle assembly 12, an elongated body portion 14, and an end effector 16. Handle assembly 12 supports a power supply, e.g., a battery assembly 18, and an ultrasonic transducer and generator assembly ("TAG") 20, although ultrasonic surgical instrument 10 may alternatively be configured as a tethered instrument wherein the power supply and generator are remote components coupled to handle assembly 12 via one or more surgical cables (not shown). Handle assembly 12 includes a rotation wheel 22, an activation button 24, and a clamp trigger 26. Battery assembly 18 and TAG 20 are each releasably coupled to handle assembly 12 and are removable therefrom to facilitate disposal of any disposable components, e.g., handle assembly 12, elongated body portion 14, and/or end effector 16, and reprocessing of any reusable components, e.g., battery assembly 18 and TAG 20.

Figure 2A:
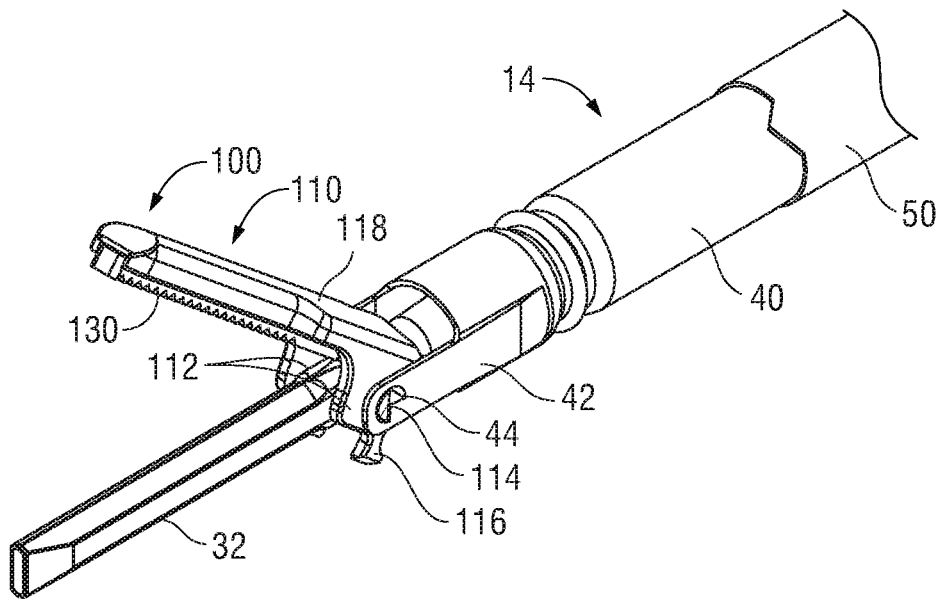
FIG. 2A is an enlarged, perspective view of a distal end portion of the ultrasonic surgical instrument of FIG. 1, wherein the end effector is disposed in the open condition and wherein a distal portion of the outer tube is removed to illustrate the components hidden thereby.
Figure 2B:
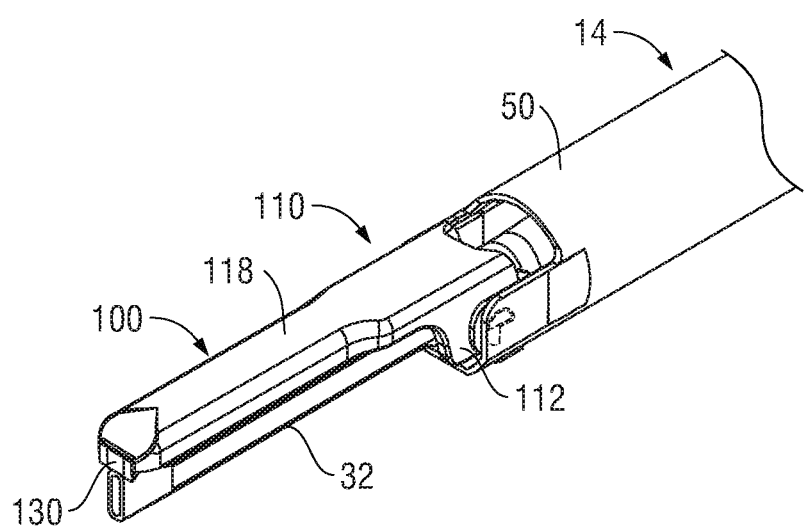
FIG. 2B is an enlarged, perspective view of the distal end portion of the ultrasonic surgical instrument of FIG. 1, wherein the end effector is disposed in a clamping condition.

With additional reference to FIGS. 2A and 2B, elongated body portion 14 includes a waveguide 30 which extends from handle assembly 12 to end effector 16. A blade 32 of end effector 16 extends distally from waveguide 30. A proximal end portion of waveguide 30 is configured to engage the ultrasonic transducer of TAG 20 to enable the transmission of ultrasonic energy along waveguide 30 from the ultrasonic transducer of TAG 20 to blade 32.

Elongated body portion 14 further includes a support frame in the form of an inner tube 40 disposed about waveguide 30 and extending between handle assembly 12 and end effector 16. Inner tube 40, more specifically, includes a proximal end portion that extends into handle assembly 12. Inner tube 40 further includes a distal end portion including a pair of spaced-apart support arms 42 (only one of which is illustrated in FIG. 2A), each defining a transverse aperture 44 therethrough. Apertures 44 are configured to pivotably receive pivot bosses 114 of proximal flanges 112 of structural body 110 of jaw member 100 of end effector 16 to pivotably engage jaw member 100 to inner tube 40 at the distal end portion thereof.

An outer tube 50 is slidably disposed about inner tube 40 and similarly extends between handle assembly 12 and end effector 16. Outer tube 50, more specifically, includes a proximal end portion that extends into handle assembly 12 and operably couples to clamp trigger 26 by way of a drive assembly (not shown), and a distal end portion defining a cut-out (not shown) that operably receives legs 116 of proximal flanges 112 of structural body 110 of jaw member 100. As a result of this configuration, clamp trigger 26 may be manipulated between an un-actuated position and an actuated position to translate outer tube 50 between an advanced position and a retracted position, thereby pivoting jaw member 100 between an open position (FIGS. 1 and 2A), wherein jaw member 100 is spaced-apart from blade 32, and a closed position (FIG. 2B), wherein jaw member 100 is approximated relative to blade 32. Alternatively, the arrangement of inner and outer tubes 40, 50, respectively, may be reversed.

Rotation wheel 22 is operably coupled to waveguide 30, inner tube 40, and outer tube 50 such that rotation of rotation wheel 22 relative to handle assembly 12 similarly rotates waveguide 30, inner tube 40, and outer tube 50 relative to handle assembly 12, thereby also rotating blade 32 and jaw member 100 relative to handle assembly 12 in a similar manner. Activation button 24 is configured to selectively activate battery assembly 18 and TAG 20 to produce ultrasonic energy that is transmitted along waveguide 30 to blade 32 of end effector 16.

As detailed above, jaw member 100 includes a structural body 110 including a pair of proximal flanges 112 which enable pivotable coupling of jaw member 100 with inner tube 40 and operable coupling of jaw member 100 with outer tube 50. Structural body 110 of jaw member 100 further includes an elongated distal portion 118 extending distally from the pair of proximal flanges 112. A jaw liner 130 is engaged with elongated distal portion 118 of structural body 110 and is positioned to oppose blade 32 such that blade 32 is inhibited from contacting structural body 110 of jaw member 100. As a result, the transfer of ultrasonic vibrations and/or thermal energy from blade 32 to structural body 110 during use is reduced. Jaw liner 130 may be formed from a compliant material, e.g., PTFE, or maybe otherwise formed.

Figure 3A:
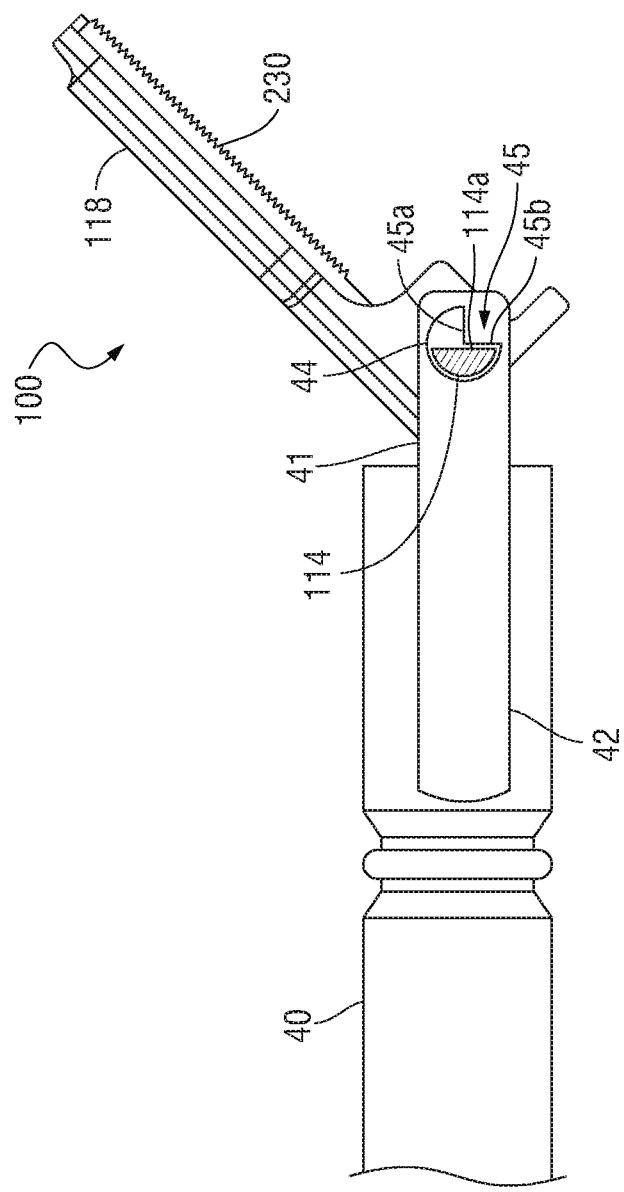
FIG. 3A is an enlarged, side view of the inner tube and jaw member of the ultrasonic surgical instrument of FIG. 1A, wherein the jaw member is disposed in the open position defined by a first interaction of a mated pivot boss and aperture.
Figure 3B:
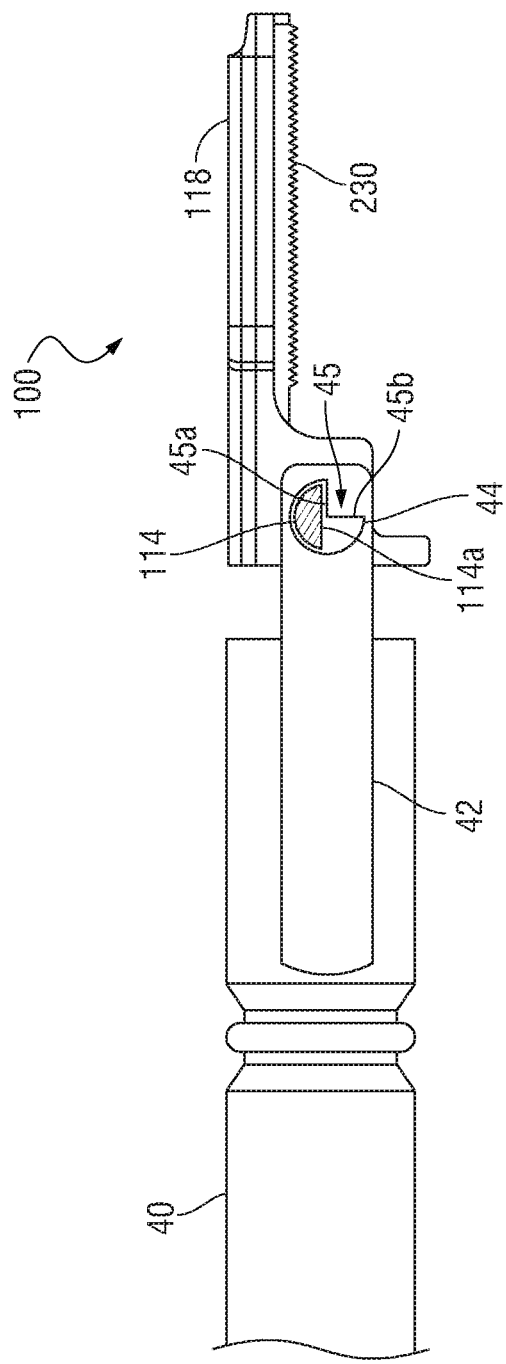
FIG. 3B is an enlarged, side view of the inner tube and jaw member of the ultrasonic surgical instrument of FIG. 1A, wherein the jaw member is disposed in the closed position defined by a second interaction of the mated pivot boss and aperture.

With additional reference to FIGS. 3A and 3B, in embodiments, the pivot bosses 114 of jaw member 110 are non-circular and include at least one flat side 114a configured to function as a stop surface to stop rotation of jaw member 100. These pivot bosses 114 are mated with non-circular apertures 44 of support arms 42 of inner tube 40 that each include at least one shelf 45 configured to function as a stop surface to prevent further closure of jaw member 100 after coming into contact with the at least one flat side 114a of each pivot boss 114. In embodiments, each pivot boss 114 is semi-circular in shape, and each of the apertures 44 is in the shape of a partial circle, e.g., a three-quarter circle, with a shelf 45 in the lower distal quadrant. Here, the shelf 45 includes first and second sides 45a, 45b respectively, and is in the form of a filled in sector configured to contact the pivot boss 114 when rotated.

When the pivot boss 114 is rotated in a clockwise direction (from the orientation illustrated in FIGS. 3A and 3B) to move jaw member 100 towards the clamping condition, the first, horizontal side 45a of the shelf 45 is positioned within the aperture 44 to impede the path of rotation beyond a certain point. More specifically, when the semi-circular pivot boss 114 is rotated in the clockwise direction to a horizontal orientation, the at least one flat side 114a of the pivot boss 114 is mated with the first, horizontal side 45a of the shelf 45. When these sides 114a, 45a of the pivot boss 114 and the shelf 45, respectively, come into contact with one another, jaw member 100 is prevented from pivoting further towards blade 32 (FIGS. 1-2B) and, thus, is maintained in the closed position. Furthermore, in order to reduce inadvertent damage to the blade 32 from the jaw member 100 and/or the jaw liner 230 from blade 32, when the jaw member 100 is maintained in the closed position, a distance is defined between the jaw liner 230 and the blade 32 to avoid the jaw liner 230 from coming into potentially destructive contact with the blade 32. The distance may be a positive gap, e.g., spacing between jaw liner 230 and blade 32 or an interference or negative gap, e.g., a distance the jaw liner 230 would move beyond the surface of blade 32 in the absence of blade 32. Providing a positive gap or an interference avoids destructive contact between the jaw liner 230 and blade 32, e.g., by maintaining space therebetween or reducing the amount the jaw liner 230 can be urged into contact with the blade 32.

Similarly, when the pivot boss 114 is rotated in the counter-clockwise direction (from the orientation illustrated in FIGS. 3A and 3B), the second, vertical side 45b of the shelf 45 is positioned within the aperture 44 to impede the path of rotation. More specifically, when the pivot boss 114 is rotated towards a vertical orientation such that the at least one flat side 114a of the pivot boss 114 is mated with the flat second vertical side 45b of the shelf 45, two flat ends 114a, 45b of the pivot boss 114 and the shelf 45, respectively, come into contact with one another preventing the jaw member 100 from pivoting further away from blade 32 (FIGS. 1-2B), thus maintaining jaw member 100 in the open position. Accordingly, as detailed above, the interaction between apertures 44 and pivot bosses 114 defines the open and closed positions of jaw member 100. A range of motion defined between the open and closed positions of jaw member 100 may be from about 70 degrees to about −20 degrees (relative to a longitudinal axis defined through apertures 44 and pivot bosses 114).

With general reference to FIGS. 1-3B, in use, ultrasonic instrument 10 is advanced into a surgical site and manipulated such that end effector 16 is positioned with tissue to be treated disposed between jaw member 100 and blade 32 with jaw member 100 disposed in the open position (FIGS. 1 and 2A). Thereafter, clamp trigger 26 is squeezed towards battery assembly 18 from the un-actuated position to the actuated position to translate outer tube 50 about inner tube 40 and relative to end effector 16, thereby pivoting jaw member 100 relative to blade 32 from the open position towards the closed position to clamp tissue between jaw member 100 and blade 32 and, more specifically, between jaw liner 130 of jaw member 100 and blade 32. Jaw member 100 is pivoted relative to blade 32 until the at least one flat side 114a of each pivot boss 114 is mated with the first, horizontal side 45a of the shelf 45 of each aperture 44, thus defining the closed position. Blade 32 may then be activated, e.g., via depression of activation button 24, to supply ultrasonic energy from TAG 20, along waveguide 30, to blade 32. The ultrasonic energy provided at blade 32 is used to treat, e.g., coagulate, cauterize, fuse, seal, cut, desiccate, fulgurate, etc., tissue clamped between jaw member 100 and blade 32.

While several embodiments of the disclosure have been described above and illustrated in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
 a support frame defining first and second non-circular apertures each defining at least one stop surface; and
 a jaw member, including:
  a structural body including a proximal flange portion and an elongated distal portion extending distally from the proximal flange portion;
  a jaw liner engaged with the elongated distal portion, the jaw liner defining a tissue-contacting surface; and
  first and second pivot bosses protruding from opposite sides of the proximal flange portion and at least partially into the first and second non-circular apertures, respectively, the first and second pivot bosses rotatable within the first and second non-circular apertures, respectively, to thereby pivot the jaw member relative to the support frame,
 wherein each pivot boss is non-circular and defines at least one stop surface configured to mate with the at least one stop surface of the respective non-circular aperture to stop rotation of the first and second pivot bosses within the first and second non-circular apertures, respectively, thereby stopping pivoting of the jaw member relative to the support frame.

2. The surgical instrument according to claim 1, wherein the support frame is an inner tube extending between a handle assembly and an end effector of the surgical instrument.

3. The surgical instrument according to claim 2, wherein the first and second non-circular apertures are defined in a pair of support arms disposed on the distal end of the support frame.

4. The surgical instrument according to claim 3, wherein the first and second non-circular apertures are coupled with the first and second pivot bosses such that the first and second pivot bosses are operably connected to the pair of support arms.

5. The surgical instrument according to claim 4, wherein the pair of support arms are spaced apart such that the first and second non-circular apertures are transversely oriented with respect to one another.

6. The surgical instrument according to claim 1, wherein the first and second non-circular apertures are configured to pivotably receive the first and second pivot bosses and to allow only partial rotation of the first and second pivot bosses when coupled.

7. The surgical instrument according to claim 1, wherein each non-circular aperture is in the shape of a partial circle with a shelf portion in the lower distal quadrant, such that the at least one stop surface of each pivot boss will come into contact with the at least one stop surface of a corresponding one of the non-circular aperture when rotated to prevent further closure of the jaw member.

8. The surgical instrument according to claim 1, wherein each pivot boss is semi-circular in shape.

9. The surgical instrument according to claim 8, wherein the first and second pivot bosses are configured to actuate the jaw member relative to an opposing structure between an open position and a closed position, such that when the first and second pivot bosses are vertically oriented the jaw member is disposed in the open position and when the first and second pivot bosses are horizontally oriented the jaw member is disposed in the closed position.

10. The surgical instrument according to claim 9, wherein a pre-determined separation exists between the jaw liner and the opposing structure when the jaw member is disposed in the closed position.

11. The surgical instrument according to claim 9, wherein an interference exists between the jaw liner and the opposing structure when the jaw member is disposed in the closed position.

12. The surgical instrument according to claim 9, wherein the opposing structure is an ultrasonic blade.

13. The surgical instrument according to claim 12, further comprising an ultrasonic waveguide extending through the support frame, wherein the ultrasonic blade is defined at a distal end of the ultrasonic waveguide.

14. A surgical instrument, comprising:
a support frame defining first and second non-circular apertures each defining at least one stop;
an ultrasonic waveguide extending through the support frame, the ultrasonic waveguide defining an ultrasonic blade extending distally from the support frame; and
a jaw member, including:
a structural body including a proximal flange portion and an elongated distal portion extending distally from the proximal flange portion;
a jaw liner engaged with the elongated distal portion; and
first and second pivot bosses protruding from opposite sides of the proximal flange portion and at least partially into the first and second non-circular apertures, respectively, the first and second pivot bosses rotatable within the first and second non-circular apertures, respectively, to thereby pivot the jaw member relative to the ultrasonic blade,
wherein each pivot boss is non-circular and defines at least one stop configured to mate with the at least one stop of the respective non-circular aperture to stop rotation of the first and second pivot bosses within the first and second non-circular apertures, respectively, beyond a pre-determined rotational position, thereby stopping pivoting of the jaw member relative to the ultrasonic blade beyond a pre-determined pivotal position, and
wherein, in the pre-determined pivotal position of the jaw member, the jaw liner and the ultrasonic blade define a gap.

15. The surgical instrument according to claim 14, wherein the at least one stop of each non-circular aperture is a stop surface.

16. The surgical instrument according to claim 15, wherein the at least one stop of each pivot boss is a stop surface.

17. The surgical instrument according to claim 14, wherein the support frame is a first tube.

18. The surgical instrument according to claim 17, further comprising a second tube configured to slide coaxially relative to the first tube, the second tube coupled to the jaw member such that sliding of the second tube relative to the first tube pivots the jaw member relative to the ultrasonic blade.

19. The surgical instrument according to claim 14, wherein the gap is a positive gap.

20. The surgical instrument according to claim 14, wherein the gap is a negative gap.

* * * * *